(12) United States Patent
Schwarz et al.

(10) Patent No.: US 12,383,678 B2
(45) Date of Patent: Aug. 12, 2025

(54) DISPLAY CONNECTION THROUGH ENERGY ACCUMULATOR COMPARTMENT ON A FLUID PUMP

(71) Applicant: B. Braun Melsungen AG, Melsungen (DE)

(72) Inventors: Jan Schwarz, Melsungen (DE); Matthias Schwalm, Schwalmstadt (DE); Carsten Niemeier, Kassel (DE); Simon Haemmerle, Kassel (DE); Christoph Erlen, Kassel (DE); Joachim Schuetz, Fulda (DE); Gerhard Schoeffel, Blaustein (DE); Daniel Wolf, Bibertal (DE)

(73) Assignee: B. Braun Melsungen AG, Melsungen (DE)

( * ) Notice: Subject to any disclaimer, the term of this patent is extended or adjusted under 35 U.S.C. 154(b) by 678 days.

(21) Appl. No.: 17/849,865

(22) Filed: Jun. 27, 2022

(65) Prior Publication Data
US 2023/0001094 A1 Jan. 5, 2023

(30) Foreign Application Priority Data
Jul. 1, 2021 (DE) ............. 20 2021 103 513.7

(51) Int. Cl.
*A61M 5/31* (2006.01)
*A61M 5/142* (2006.01)

(52) U.S. Cl.
CPC ....... *A61M 5/31* (2013.01); *A61M 2005/3125* (2013.01); *A61M 2205/8206* (2013.01)

(58) Field of Classification Search
CPC .. A61M 5/142; A61M 5/14244; A61M 5/145; A61M 5/1456; A61M 2005/14268; A61M 2005/14272; A61M 2205/121; A61M 2205/122; A61M 2205/82; A61M 2205/8206
See application file for complete search history.

(56) References Cited

U.S. PATENT DOCUMENTS

| | | | |
|---|---|---|---|
| 11,090,435 B2 * | 8/2021 | Day ................. | A61M 5/31525 |
| 2012/0136325 A1 * | 5/2012 | Allen ................. | A61M 39/22 |
| | | | 604/319 |

(Continued)

FOREIGN PATENT DOCUMENTS

| | | | | |
|---|---|---|---|---|
| EP | 3253431 B1 | 11/2018 | | |
| EP | 3920317 A1 * | 12/2021 | ............... | A62B 9/04 |

(Continued)

OTHER PUBLICATIONS

Search Report received in German Application No. 20 2021 103 513.7 dated Jun. 9, 2022, with translation, 6 pages.

*Primary Examiner* — Rebecca E Eisenberg
(74) *Attorney, Agent, or Firm* — Christopher A. Rothe; CM Law

(57) ABSTRACT

A medical fluid pump having a housing which encloses an interior space. The housing includes an upper housing shell, a lower housing shell and a front flap pivotally articulated on the housing. An opening of an energy accumulator compartment is formed on the lower housing shell. The energy accumulator compartment is provided and designed to receive an energy accumulator. The energy accumulator compartment comprises a cutout or aperture opening toward the interior space.

7 Claims, 5 Drawing Sheets

(56) References Cited

U.S. PATENT DOCUMENTS

| | | | | |
|---|---|---|---|---|
| 2013/0338635 A1* | 12/2013 | O'Connor | ......... | A61M 5/14244 |
| | | | | 604/506 |
| 2016/0106910 A1* | 4/2016 | Yap | ................... | A61M 5/14244 |
| | | | | 73/865.8 |
| 2021/0146033 A1* | 5/2021 | Smith | ................. | H01M 50/502 |

FOREIGN PATENT DOCUMENTS

| | | | | |
|---|---|---|---|---|
| JP | 3143246 U | 7/2008 | | |
| WO | WO-2015127965 A1 * | 9/2015 | ........ | A61M 5/14216 |

\* cited by examiner

DISPLAY CONNECTION THROUGH ENERGY ACCUMULATOR COMPARTMENT ON A FLUID PUMP

CROSS-REFERENCE TO RELATED APPLICATION

This application claims priority under 35 U.S.C. § 119 to German Application No. 20 2021 103 513.7, filed Jul. 1, 2021, the content of which is incorporated by reference herein in its entirety.

FIELD

The present disclosure relates to a medical fluid pump having a cutout or aperture in an energy accumulator compartment.

BACKGROUND

In the medical field, fluid pumps, in particular syringe pumps and peristaltic pumps, are widely used to supply a patient with a defined dose of medication. In order to ensure access to, for example, electronic components of the fluid pump for service purposes, the fluid pump is provided, for example, with at least one additional service opening on a housing part. This has the disadvantage that the at least one service opening must be protected against the ingress of foreign bodies and liquids in order to prevent damage to the electronics. Such protection is associated with additional manufacturing effort and additional manufacturing costs and additionally represents a possible source of error.

Alternatively, it is possible to design the fluid pump without a service opening. This has the consequence that the fluid pump must be completely opened in the event of a defect in a component. This means that at least one upper housing shell and one lower housing shell must be separated from each other, which is associated with increased effort for the service technician.

SUMMARY

Therefore, the object of the present disclosure is to provide accessibility to electronic components in the interior of a fluid pump without providing an additional opening on a housing of the fluid pump and without having to open the fluid pump completely.

This object is achieved by the fluid pump according to the disclosure with a cutout or aperture in an energy accumulator compartment.

Accordingly, the medical fluid pump has a housing consisting of an upper housing shell and a lower housing shell as well as a front flap pivotably articulated on the housing, preferably on the lower housing shell. On the lower housing shell, an opening of an energy accumulator compartment separated from the housing's interior space is formed, which is provided and designed to receive an energy accumulator, wherein the energy accumulator compartment comprises a cutout or aperture opening toward the housing's interior space, preferably formed in the direction toward the upper housing shell.

In other words, the fluid pump has the housing including the upper housing shell and the lower housing shell. The front flap is articulated on the lower housing shell and preferably includes operating elements and/or a display device. The lower housing shell further comprises an energy accumulator compartment. The energy accumulator compartment is provided and designed to accommodate an energy accumulator, in particular completely. In yet other words, the energy accumulator compartment is fully integrated into the lower housing shell of the fluid pump. The energy accumulator is preferably an accumulator or a battery. However, other types of energy accumulators for electrical energy such as a capacitor are also conceivable.

The energy accumulator compartment has an opening facing outwards, which allows an energy accumulator to be inserted into the fluid pump from outside. This opening is preferably located on the underside of the fluid pump. A cutout or aperture (window) is provided and formed on the inner wall of the energy accumulator compartment opposite the opening or on a side wall of the energy accumulator compartment extending laterally to the opening.

The cutout or aperture ensures that, when the energy accumulator is removed, reaching/accessing an interior/interior space of the fluid pump is possible without detaching the upper housing shell and the lower housing shell from each other and without having to provide an additional service opening on the housing.

In a first aspect, the cutout or aperture is a service access to electronic components of the medical fluid pump.

In other words, the cutout or aperture is designed as a service access that allows reaching/accessing electronic components inside the medical fluid pump when the energy accumulator is removed. Thus, the electronic components can be inspected, serviced and/or replaced through the cutout or aperture in the energy accumulator compartment without disconnecting the upper housing shell and the lower housing shell and without having to provide an additional service opening on the housing.

In a further aspect, the electronic component is a circuit board and at least one connecting cable connecting the front flap and the circuit board. A plug connector on the circuit board, provided and designed for receiving a connector of the connecting cable, and the cutout are aligned relative to each other such that they are arranged on the same normal to a plane which is oriented parallel to the upper housing shell and the lower housing shell.

In other words, the one electronic component is a circuit board that preferably includes essential control devices of the fluid pump. In particular, the circuit board is connected to the front flap, which includes operating and display devices, by means of a connecting cable. The connecting cable is connected to the circuit board by means of a plug connector formed on the circuit board. The plug connector and the cutout or aperture are oriented with respect to each other in such a way that the opening of the energy accumulator compartment, the cutout or aperture and the plug connector are in alignment/arranged on a straight line, the straight line preferably being oriented perpendicular to the bottom side and/or a top side of the housing.

By arranging the plug connector and the cutout or aperture in relation to each other as described above, it is possible to reach the plug connector without separating the upper housing shell from the lower housing shell and without forming an additional service opening in an outer shell of the fluid pump. This increases the ease of repair and service, especially when replacing the front flap and/or operating and display devices contained in the front flap, and at the same time reduces the risk of emerging leaks during service work.

In a further aspect, the cutout or aperture has dimensions which correspond at least to the dimensions of the connector.

In other words, the cutout or aperture is dimensioned such that the connector can be passed through the cutout or aperture without tilting the connector. Preferably, the cutout or aperture is dimensioned such that, in addition to the connector, fingers of a service technician can reach through the cutout or aperture to release the connector from the plug connector. In particular, the cutout or aperture preferably has dimensions of approximately 20 mm×50 mm.

Such a dimensioning of the cutout or aperture allows servicing of the electronic components without separating the upper housing shell from the lower housing shell and without the need for the service technician to use special tools such as adapted tweezers or pliers.

In another aspect, the dimensions of the opening of the energy accumulator compartment are larger than the dimensions of the cutout or aperture.

In other words, the opening area of the energy accumulator compartment is larger than the cutout or aperture area.

This prevents the inserted energy accumulator from falling through the cutout or aperture and damaging the electronic components. In addition, it makes it easier for the service technician to access the electronic components.

In another aspect, the cutout or aperture is closed with a service flap.

In other words, the service flap is provided and designed to releasably/reversibly close the cutout or aperture. The service flap can be attached to the cutout or aperture with locking mechanisms or screws. This prevents access to the electronic components in an embodiment in which it is envisaged that an end customer replaces the energy accumulator by himself.

In another aspect, the lower housing shell and the energy accumulator compartment are formed in one piece.

In other words, the energy accumulator compartment as a part of the lower housing shell is in particular made of one material. The lower housing shell having the energy accumulator compartment is preferably made by injection molding.

In a further aspect, the medical fluid pump is provided with a lid that is provided and designed to close the opening of the energy accumulator compartment and in particular to be flush with the lower housing shell.

In other words, the lid is provided and designed to seal/close off the energy accumulator compartment and thus an interior space of the fluid pump from the environment. In this context, the lid is designed in such a way that when the lid closes the opening, a flat surface is created with an outer surface/outer skin of the lower housing shell.

The lid prevents the inserted energy accumulator from falling out of the energy accumulator compartment, on the one hand, and foreign bodies from entering the interior of the fluid pump, on the other hand. The flat outer surface of the lower housing shell improves the handling and the haptic properties of the fluid pump.

In another aspect, the lid has a circumferential seal on its inner surface that seals the lid against a sealing surface formed in the lower housing shell.

In other words, a seal is provided and formed on the surface of the lid that faces inwardly in a condition in which the lid closes the opening, and completely surrounds the opening in the condition in which the lid closes the opening. A sealing surface is provided and formed on the lower housing shell that completely surrounds the opening against which the lid seals by means of the seal in an assembled state.

The seal completely surrounding the opening ensures that even in a damp or wet operating environment, moisture cannot penetrate the fluid pump and damage electronic components such as the energy accumulator in particular.

In another aspect, the lid is fixed to the lower housing shell of the medical fluid pump with screws, wherein covering caps are provided and designed to cover heads of the screws (screw heads) in an assembled state and in particular to be flush with the lid.

In other words, tapped holes/threaded holes/threads are formed in the lower housing shell into which the screws are screwed and fix the lid to the lower housing shell. Through-holes for the screws are formed in the lid. On the outer surface of the lid, preferably cylindrical countersinks are provided and formed around the through-holes. These cylindrical countersinks are designed to accommodate covering caps preferably in a force-fit manner. In a state inserted into the countersinks, the covering caps are flush with the outer surface of the lid. The covering caps are preferably formed from an elastic material such as rubber. Preferably, the covering caps are provided and designed to be removed in a destructive manner.

The covering caps prevent dirt and moisture from entering the screw opening. In particular, the covering caps prevent moisture from entering the interior of the fluid pump through the through-holes in the lid past the screw. Furthermore, the covering caps prevent unauthorized persons from opening the lid. The closed, flat surface further improves the handling and haptic properties of the fluid pump.

In another aspect, the energy accumulator compartment includes a depression provided and designed to receive an energy accumulator connection cable.

In other words, the energy accumulator compartment includes a depression that allows the energy accumulator connection cable connecting the energy accumulator to consumers of the fluid pump and preferably to a line voltage supply to be routed in a predetermined manner.

A separately formed depression for the energy accumulator connection cable prevents the energy accumulator cable from being damaged or pulled out of a connector when the fluid pump is moved.

In another aspect, the extension of the energy accumulator compartment from the lower housing shell toward the upper housing shell is larger than the extension of the energy accumulator compartment from the front flap toward a pump rear side opposite the front flap.

In other words, the extension of the energy accumulator compartment in the direction from a fluid pump bottom side toward a fluid pump top side is larger than the extension of the energy accumulator compartment in the direction from a fluid pump front side toward a fluid pump rear side. The fluid pump bottom side is preferably provided with pedestals. The fluid pump front side is preferably provided with an operating panel.

In a further aspect, the energy accumulator compartment comprises a recess oriented in the direction of the front flap.

In other words, the energy accumulator compartment is provided with a material recess in a direction parallel to the front flap or normal to the fluid pump bottom side.

The recess allows easy removal of the energy accumulator by a service technician, for example. In addition, the recess provides better air circulation around the energy accumulator, which ensures that the energy accumulator does not heat up excessively during discharging and/or charging.

In another aspect, at least one buffer element is provided and formed on the lid on the side facing the energy accumulator compartment.

In other words, at least one elastic buffer element is attached to the inside of the lid. In the process of mounting the lid on the underside of the housing, the elastic buffer element is compressed between the lid and the energy accumulator. Preferably, the buffer element is provided and designed as a foam bead.

The buffer element holds the energy accumulator in position and absorbs shocks and vibrations, which protects the energy accumulator from external forceful impact, for example if the fluid pump falls.

BRIEF DESCRIPTION OF THE DRAWING FIGURES

DETAILED DESCRIPTION

Figure 1:
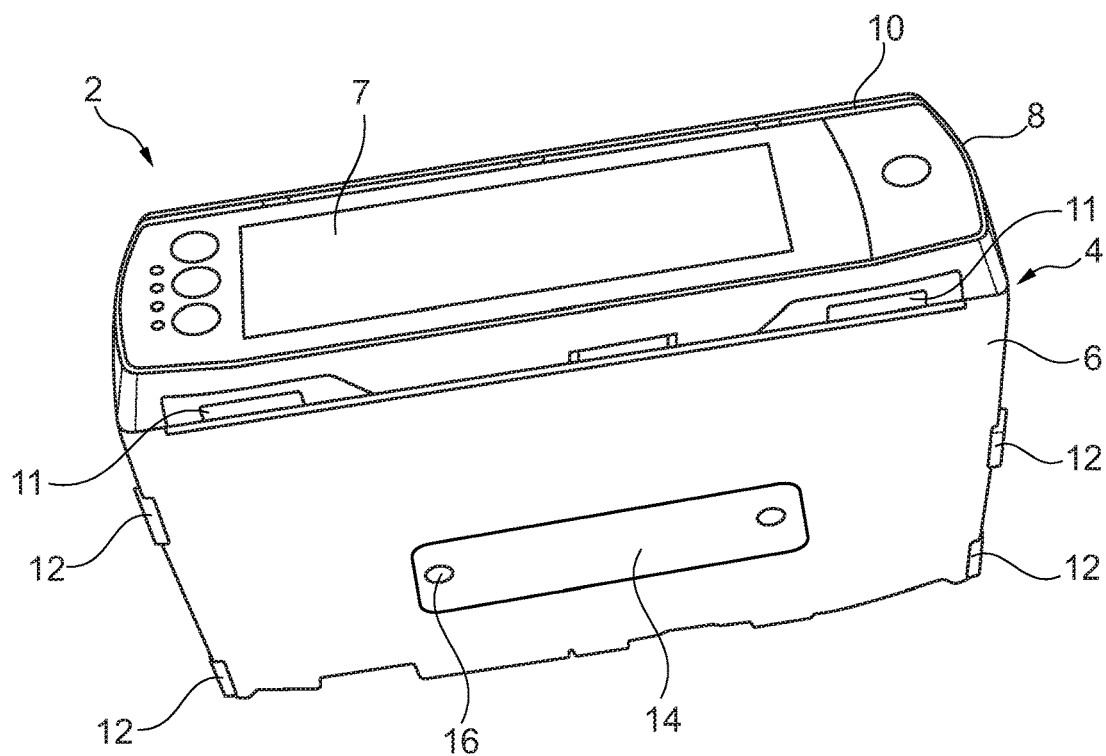
FIG. 1 is a perspective view of a medical fluid pump according to the disclosure.

FIG. 1 shows a medical fluid pump 2 according to the disclosure having a housing 4 which includes a lower housing shell 6 and an upper housing shell 8. At a front side of the fluid pump 2, a front flap 10 is designed, which is articulated to the lower housing shell 6 in a foldable manner via hinges 11 and is provided and designed to contain an operating and display element 7 of the fluid pump 2. On an underside of the fluid pump 2 formed by the lower housing shell 6, pedestals 12 and a lid 14 of an energy accumulator compartment (20 in FIG. 2) are formed. The lid 14 is flush with the underside of the fluid pump 2. Covering caps 16 are formed on the lid 14.

Figure 2:
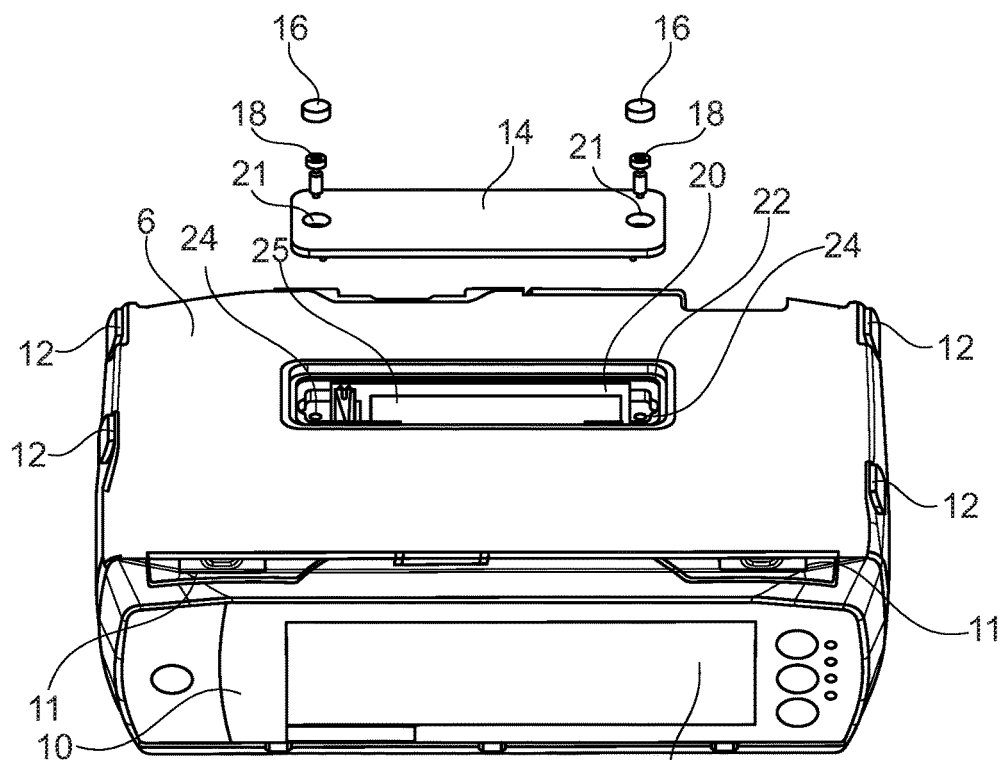
FIG. 2 is a perspective view of the medical fluid pump according to the disclosure with an opened lid of an energy accumulator compartment.

FIG. 2 shows the medical fluid pump 2 in a state in which the lid 14 of the energy accumulator compartment 20 is open. The lid 14 can be attached to the fluid pump 2 via screws 18, or can be/is attached to the fluid pump 2 via screws 18 such that an opening of the energy accumulator compartment 20 is closed. The lid 14 includes cylindrical countersinks 21 on an outer surface (a surface facing away from the energy accumulator compartment 20 in an assembled state), which are provided and designed to receive the covering caps 16. Here, the cylindrical countersinks 21 are located above through-holes 23 of the lid 14, through which the screws 18 are screwed to attach the lid 14 to the fluid pump 2. The covering caps 16 prevent moisture and contaminants from entering the interior of the fluid pump 2 through the through-holes 23. The energy accumulator compartment 20 includes a surrounding sealing rim/sealing face 22 and threaded holes 24 into which the screws 18 can be screwed. An energy accumulator 25 is inserted in the energy accumulator compartment 20.

Figure 3:
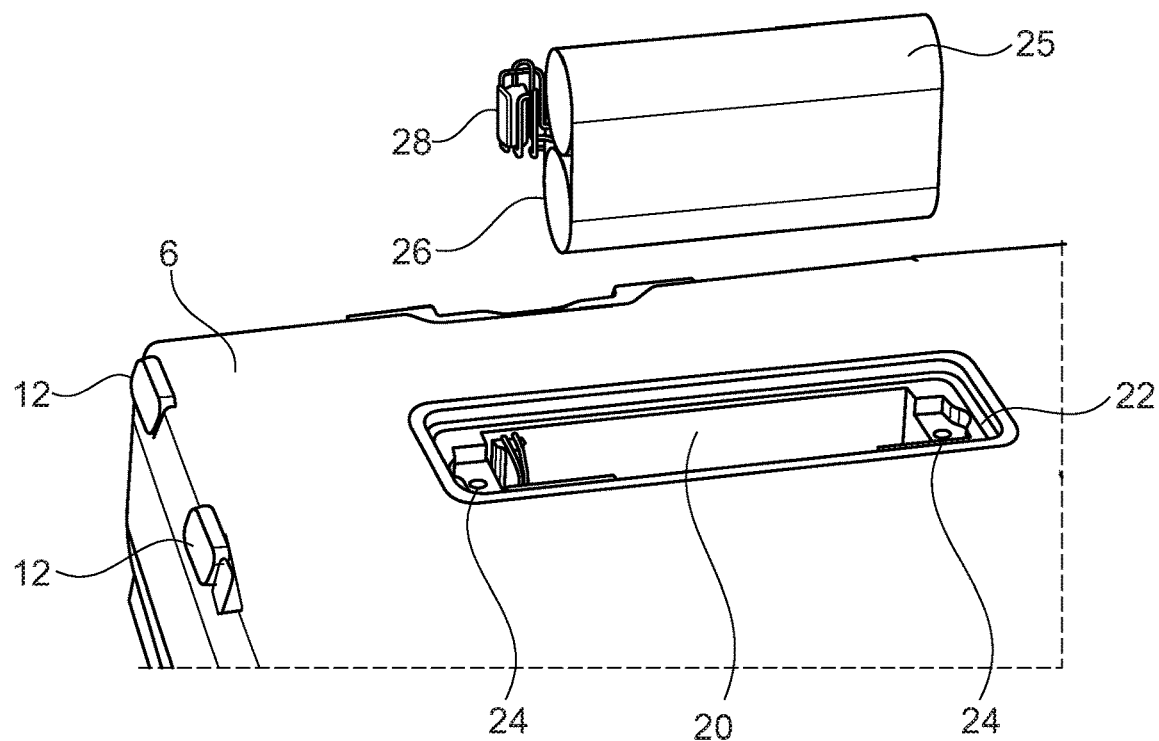
FIG. 3 shows a detailed view of the medical fluid pump according to the disclosure with an energy accumulator removed.

FIG. 3 shows a detailed view of the bottom side of the lower housing shell 6 together with the opening of the energy accumulator compartment 20 and the removed energy accumulator 25. In a preferred embodiment, the energy accumulator 25 is a rechargeable battery which, when the fluid pump 2 is connected to a mains voltage supply, is charged with mains voltage and, when the fluid pump 2 is disconnected from the mains voltage, supplies the fluid pump 2 with energy. Preferably, the energy accumulator 25 is constructed from a plurality of energy accumulator elements 26 and is connected to the electronics of the fluid pump 2 by means of a power supply connector 28. Preferably, the energy accumulator compartment 20 is arranged in the fluid pump such that, in an installed state, the energy accumulator 25 extends to a larger extent/further in a direction normal to the underside of the fluid pump 2 than in the direction of the underside of the fluid pump 2.

Figure 4:
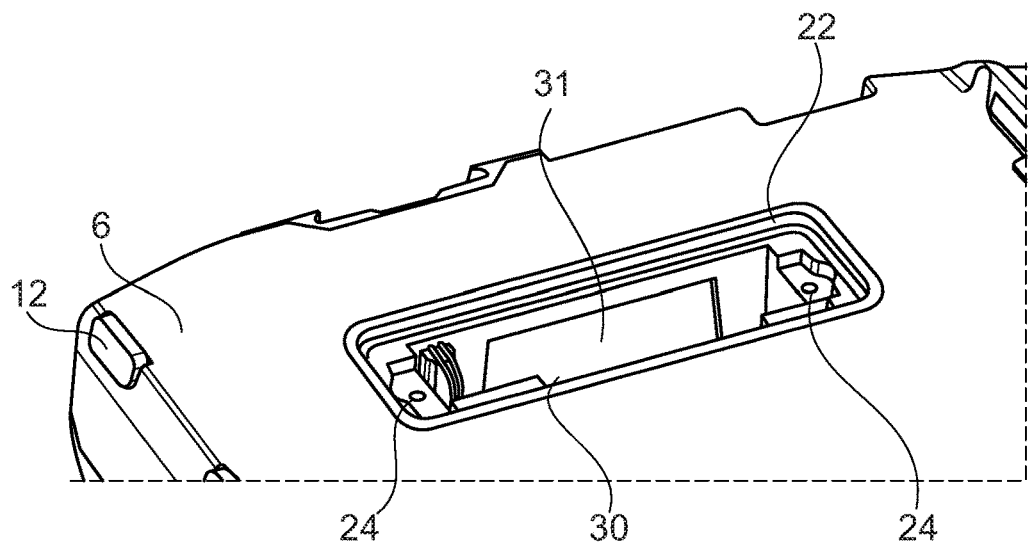
FIG. 4 shows a detailed view of the medical fluid pump according to the disclosure.

FIG. 4 shows a detailed view of the underside of the lower housing shell 6 together with the opening of the energy accumulator compartment 20. In the direction of the front flap 10, the energy accumulator compartment has a recess 30. On the side facing away from the front flap 10, the energy accumulator compartment 20 has a cutout 31. The recess 30 and the cutout 31 ensure that air reaches the sides of the installed energy accumulator 25 and that the energy accumulator 25 is air-cooled in this way. In addition, the recess 30 facilitates removal of the installed energy accumulator 25.

Figure 5:
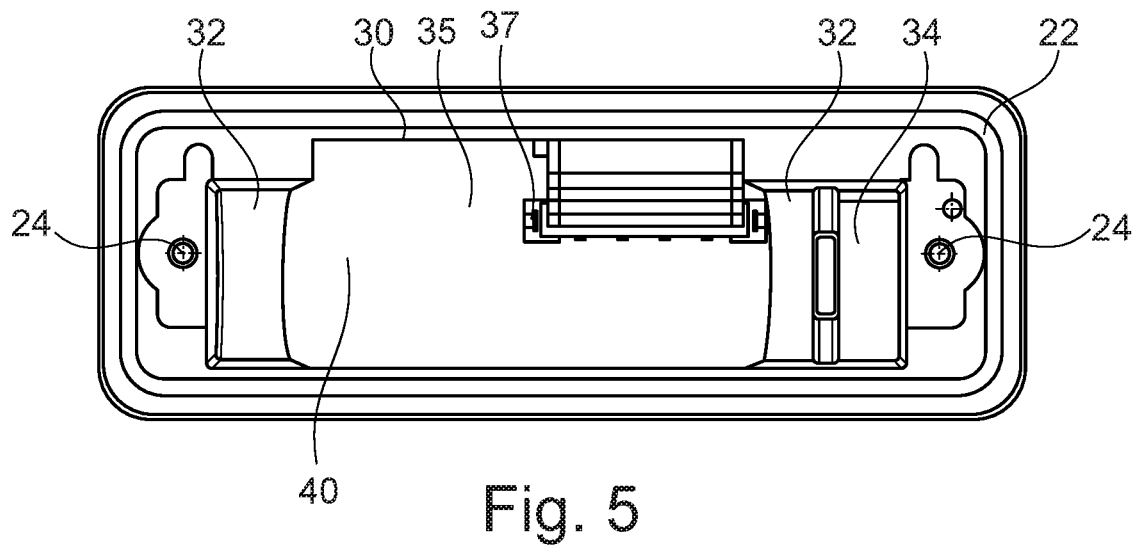
FIG. 5 shows a top view of the energy accumulator compartment of the medical fluid pump according to the disclosure.

FIG. 5 shows a top view of the energy accumulator compartment 20 of the fluid pump 2. The energy accumulator compartment 20 includes an energy accumulator receiving portion 32 formed on the side of the energy accumulator compartment facing away from the opening of the energy accumulator compartment 20. The energy accumulator receiving portion 32 is provided and designed to receive the energy accumulator 25. Preferably, the shape of the energy accumulator receiving portion 32 is adapted to the contour of the energy accumulator 25. The energy accumulator compartment 20 has a depression 34 which is provided and designed to receive the power supply connector 28 that connects the electronics of the fluid pump 2 to the energy accumulator 25. On the side of the energy accumulator compartment 20 facing away from the opening of the energy accumulator compartment 20, the cutout or aperture 35 is provided and formed. Through the cutout or aperture 35, a plug connector 37 arranged behind the cutout or aperture 35 as viewed from the direction of the opening of the energy accumulator compartment 20 is formed on a circuit board 40.

Figure 6:
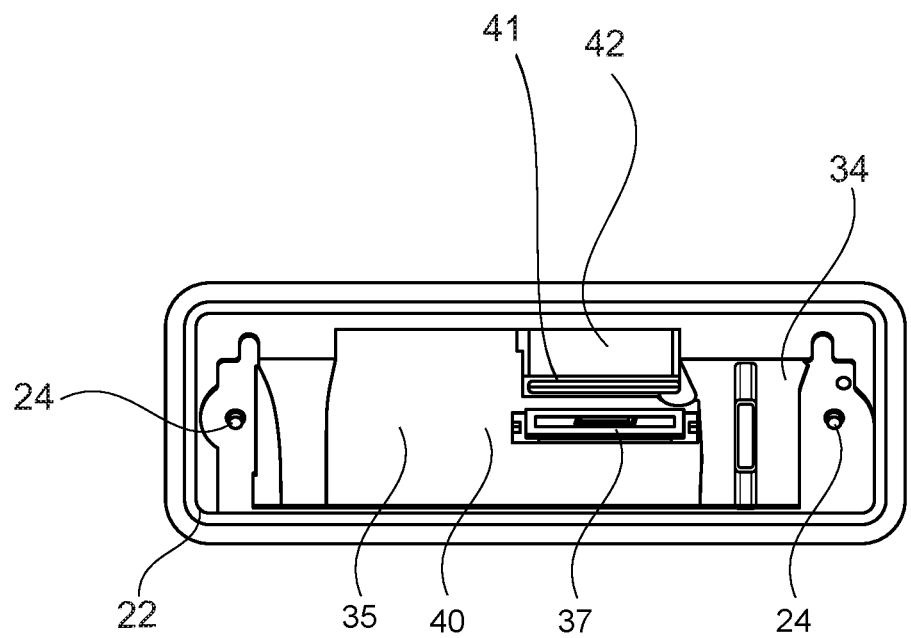
FIG. 6 shows a top view of the energy accumulator compartment of the medical fluid pump according to the disclosure.

FIG. 6 shows a top view of the energy accumulator compartment 20 of the fluid pump 2 in a state in which the connector 41 of a connecting cable 42 and the plug connector 37 of the circuit board 40 are disconnected. The circuit board preferably includes at least one control device of the fluid pump 2. The connecting cable 42 has its other end connected to the front flap 10 and connects the operating and display devices included in the front flap 10 to the circuit board 40. Via the connecting cable 42, any inputs that an operator makes by means of the operating device included in the front flap 10 are transmitted to the circuit board 40 or to the control device of the circuit board 40 included in the circuit board 40, and outputs are transmitted from the circuit board 40 to the display device of the front flap 10.

Figure 7:
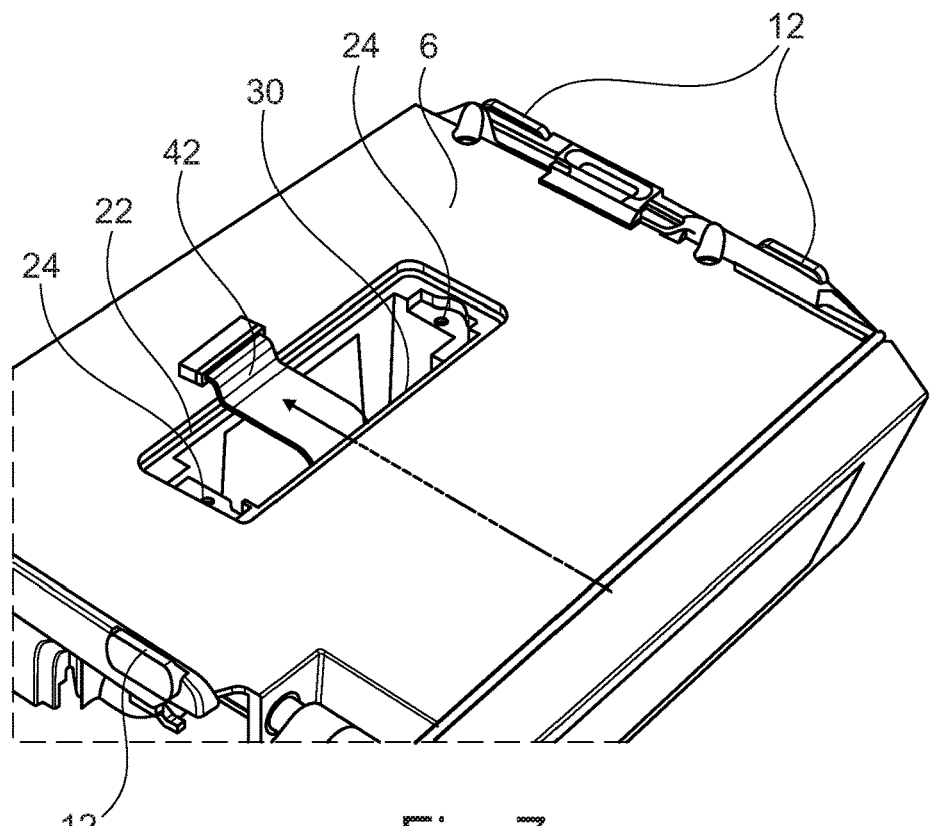
FIG. 7 shows a perspective view of the fluid pump in a state in which a connecting cable is disconnected from a circuit board.

FIG. 7 shows an assembly procedure of the connecting cable 42. The connecting cable 42 can be disconnected from the plug connector 37 through the cutout or aperture 35, for instance in case of a defect of the front flap 10, without completely opening the housing 4 of the fluid pump 2 or separating the upper housing shell 8 and the lower housing shell 6 from each other. When a new front flap 10 is then mounted on the housing 4 of the fluid pump, the connecting cable 42 can be inserted through the cutout or aperture 35 into the plug connector 37.

Figure 8:
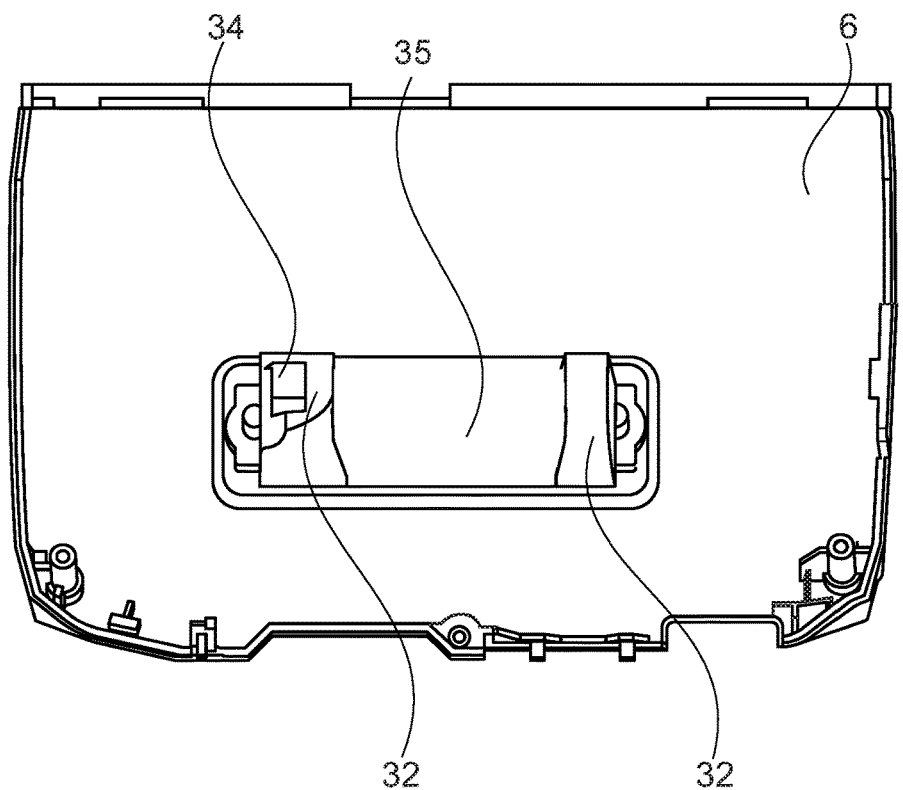
FIG. 8 shows an interior view of a lower housing shell of the medical fluid pump according to the disclosure.

FIG. 8 shows an interior view of the lower housing shell 6 of the medical fluid pump 2 according to the disclosure. The energy accumulator compartment 20 is formed integrally with the lower housing shell 6 and extends substantially normal to the lower housing shell 6.

Figure 9:
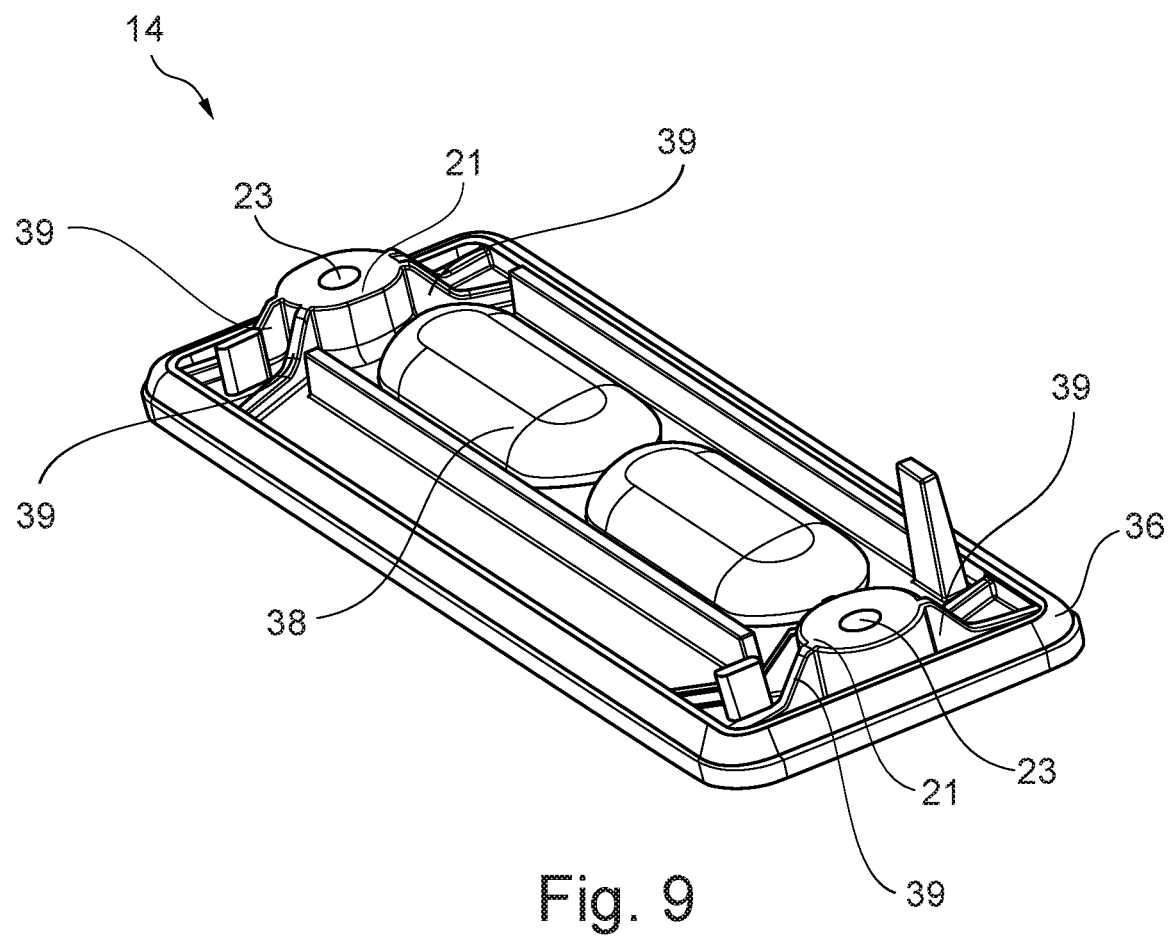
FIG. 9 shows the lid of the energy accumulator compartment.

FIG. 9 shows the lid 14 of the energy accumulator compartment 20, in particular the inner side of the lid 14 of the energy accumulator compartment 20. The inner side of the lid 14 is to be understood as the side oriented toward the interior space of the fluid pump 2 in a state in which the lid 14 is mounted to the fluid pump 2. On the inner side, a seal 36 is circumferentially provided and designed to seal the lid 14 against the sealing rim 22 of the energy accumulator compartment 20 in a mounted state. Further, buffer elements 38 are provided and formed on the inner side. The buffer elements 38 are preferably foamed buffer elements 38 in the form of foam beads. If the lid 14 is screwed against the housing 4 of the fluid pump 2 by means of the screws 18 passing through the through-holes 23, the seal 36 is pressed against the sealing rim 22 and thus forms a sealing. Furthermore, the buffer element 38 is pressed/clamped against the energy accumulator 25 in an assembled state and fixes the energy accumulator 25 between the lid 14 and the energy accumulator receiving portion 32. Thus, slipping of the energy accumulator 25 in the energy accumulator compartment 20 can be prevented and the buffer elements 38 protect the energy accumulator 25 from mechanical stress. The countersinks 21 are supported by means of struts 39 in the direction toward the circumferential seal 36. In particular, the struts 39 are oriented in the direction toward the corner sections of the surrounding seal 36. This ensures uniform application of force by the screws 18, particularly in the corner sections of the circumferential seal 36, and further impedes the penetration of liquids.

The invention claimed is:

1. A medical fluid pump comprising:
a housing which encloses an interior space;
an upper housing shell;
a lower housing shell; and
a front flap pivotally articulated on the housing,
the housing comprising an energy accumulator compartment,
an opening for the energy accumulator compartment being formed on the lower housing shell,
the energy accumulator compartment being configured to receive an energy accumulator, and
the energy accumulator compartment comprising a cutout or aperture that opens toward the interior space wherein the cutout or aperture is a service access to electronic components of the medical fluid pump.

2. The medical fluid pump of claim 1,
wherein the electronic components comprise a circuit board and a connecting cable connecting the front flap and the circuit board, and
wherein a plug connector on the circuit board, provided and designed for receiving a connector of the connecting cable, and the cutout or aperture are aligned relative to each other such that the plug connector and the cutout or aperture are arranged on a same normal to a plane which is oriented parallel to the upper housing shell and the lower housing shell.

3. The medical fluid pump of claim 2, wherein the cutout or aperture has dimensions which correspond at least to dimensions of the connector of the connecting cable.

4. The medical fluid pump of claim 1, wherein dimensions of the opening for the energy accumulator compartment are larger than the dimensions of the cutout or aperture.

5. The medical fluid pump of claim 1, wherein the cutout or aperture is closed with a service flap.

6. The medical fluid pump of claim 1, wherein the cutout or aperture is formed in a direction toward the upper housing shell.

7. The medical fluid pump of claim 1, wherein the front flap is pivotally articulated on the lower housing shell of the housing.

* * * * *